United States Patent [19]

Josowicz et al.

[11] Patent Number: 5,254,223

[45] Date of Patent: Oct. 19, 1993

[54] PROCESS FOR MAKING SEMIPERMEABLE POLYMERS WITH ION EXCHANGE AND ION CONDUCTIVE CAPABILITIES ON AN ELECTRICALLY CONDUCTIVE SUBSTRATE

[76] Inventors: Mira Josowicz, Hohenzollernstrabe 49, 8000 Munchen; Karin Potje-Kamloth, Putzbrunnerstr. 12, 8012 Ottobrunn, both of Fed. Rep. of Germany

[21] Appl. No.: 933,490

[22] Filed: Aug. 21, 1992

[51] Int. Cl.$^5$ ................................. C25B 3/10
[52] U.S. Cl. .................... 204/59 R; 204/72; 204/78; 522/20
[58] Field of Search .......... 204/59 R, 78, 72; 522/20, 63, 69, 151, 153, 154; 521/25, 27; 205/58, 167, 182; 427/384

[56] References Cited

U.S. PATENT DOCUMENTS

| | | | |
|---|---|---|---|
| 3,335,075 | 8/1967 | Borman | 204/59 R |
| 4,334,054 | 6/1982 | Dubois et al. | 204/59 R |
| 5,112,450 | 5/1992 | Jasne | 204/59 R |
| 5,133,841 | 7/1992 | Higo et al. | 204/59 R |

*Primary Examiner*—John Niebling
*Assistant Examiner*—Patrick J. Igoe
*Attorney, Agent, or Firm*—Thorpe, North & Western

[57] ABSTRACT

The process for preparation of semipermeable polymer layers with ion-exchanging and ion-conducting capabilities comprises the steps of making and depositing a polymer layer in situ by electrochemical polymerization on an electrically conductive substrate and subsequently cross-linking, by heating or irradiating. The electrochemically formed polymer layers are built up of poly(oxyphenylene) or poly(naphthylene) chains, in which the aromatic units contain the ion-exchanging and ion-conducting groups. These polymer layers are suitable for use as a semipermeable membrane in an electrode/membrane unit, as a selective layer or as a component of a selective layer of potentiometric and amperometric sensors and as a solid polymer electrolyte in electrochemical cells.

16 Claims, No Drawings

PROCESS FOR MAKING SEMIPERMEABLE POLYMERS WITH ION EXCHANGE AND ION CONDUCTIVE CAPABILITIES ON AN ELECTRICALLY CONDUCTIVE SUBSTRATE

BACKGROUND OF THE INVENTION

The present invention relates to a semipermeable polymer layer, which is semipermeable to charge carriers and/or permeable to neutral species, and more particularly to a process of its manufacture in front of or overlying an electrically conductive substrate, and its use and application.

Placing the semipermeable polymer layer as a membrane in front of an electrically conductive substrate is generally known. The determinant membrane behavior to separate charge carriers or/and to be permeable to neutral species is governed by its structure and different driving forces involved in use of the membrane. An incorporation of ion exchanging and ion-conducting components into an individual polymer chain of the membrane allows for selecting a chemical species to be separated from other species; the permeability of the polymer layer further limits passage of the species through the membrane to only one kid of charge carried by the species. The incorporated ion-exchanging and ion-conducting components which are carrying a charge themselves are known as fixed sites. For each charge of the fixed sites, there is a corresponding counterion, which is present in the membrane. The separation capability of the membrane is based on the exchange or counterions with ions of the same polarity present in the solution (adjacent the membrane containing the species to be "separated"). Simultaneously, the exchange of co-ions of the same polarity as the fixed sites is prohibited. Therefore the passage of the co-ions through the membrane is suppressed.

It is desirable that such polymer layers be made pinhole free, chemically inert and show high mechanical stability. Furthermore, the permeation and the exchange procedure or species should be carried out with high selectivity and high velocity.

The application of polymer layers of prior art showing ion exchange and ion conducting properties of a membrane is based on two distinct manufacturing steps:

1. The preparation of an ion exchange resin.

The ion exchange resin is made by chemical polymerization or polycondensation. Such procedures provide a direct incorporation of ionic groups (fixed sites) into the polymer. When chemical mixed polymerization of styrene and divinylbenzene is used, a successively applied chemical introduction of ionic groups is required (F. Helfferich; Ionenaustauscher, Verlag Chemie, Weinheim, 1959).

2. The crocessino of the ion exchange resin to a semipermeable membrane.

The processing is carried out either by dissolving in an appropriate solvent only the ion-exchange resin or a mixture of the ion exchange resin and a binder (referred to as matrix —i.e. polystyrene, polyvinylchloride or polyethylene). The membrane is mechanically attached to the electrically conductive substrate by cast coating procedures, i.e., dip-coating or spring-coating processes. After the solvent evaporation, the polymer remains on the substrate and can subsequently be used as a membrane. Such membranes currently used are made, e.g., of Nafion, a perfluorinated polymer, containing sulfonic groups (Wilson A. d., Prosser H. J. (Eds.); Developments in Ionic Polymers, Elsevier; Vol 2, London, 1983). They are capable of exchanging cations.

The transport of species to be separated through the membrane is a kinetically slow process. Therefore, the permeation of the species through the polymer layer is dependent upon the thickness of the layer. This fact makes the layer thickness an important variable for the permeation rate, which up to now could be exploited only in a limited way by applying casting techniques of prior art. Furthermore, the thickness of membrane layers manufactured by techniques of prior art is strongly dependent on the nature of the electrode surface to be coated. For example, using non pretreated and consequently rough substrate surfaces, the cast layers exhibit a relatively broad thickness range of at least 0.05 mmm to 0.1 mm due to the conditions of their preparation. Consequently, the fabrication of uniform membranes of thicknesses lower than that mentioned above is not feasible. A polished and consequently very smooth surface of the substrate enables the fabrication of uniform layers of thickness of about 200 nm. However, in that case, the thickness of the membrane is dependent upon the nature of the required solvent which is used for the processing of the precursor materials.

With decreasing layer thickness of the polymer the possibility of creating pores and cracks increases. The polymer layer thus loses its unique and advantageous membrane property of separating charges of the permeating species. It is known that the membrane diffusion coefficients of species to be separated by such polymer-coated electrodes are lowered by a magnitude of three to four orders of magnitude when compared to those in the electrolyte solution. Therefore, the hitherto process for making a semipermeable polymer on the electroactive surface of the substrate yields a product with limited application and usefulness. (Espenscheid M. W., Ghatak-Roy A. R., Moore III R. B. et al., J. Chem. Soc., Faraday Trans. 1, 82 (1986) 1051-70.)

SUMMARY OF THE INVENTION

Accordingly, it is an object of our invention to provide a process of manufacturing, on conducting surfaces, a semipermeable polymer layer with ion exchange and ion conducting capabilities, which preferentially leads to thinner polymer layers (with thicknesses in submicrometer range) and which allows for a high exchange rate of species to be separated. The advantages of the procedure particularly are that the preparation of the polymer which exhibits ion-exchanging and ion-conducting properties is carried out in one processing step with high productivity, reproducibility, all of which is independent of the nature of the substrate surface upon which the polymer layer is disposed. The polymer layers are developed to provide a pinhole free membrane.

In keeping with this object and with others which will become apparent hereinafter, our process comprises the steps of making a semipermeable polymer from an electrolyte bath by electrochemical polymerization of OH-containing aromatic monomers with acidic or basic functionalized groups or alternatively by copolymerization or mixed polymerization of said aromatic monomers with noncross-linkable or cross-linkable OH-containing monomers, respectively. The polymer is then deposited in situ on the electrically conductive substrate and subsequently cross-linked. The OH-containing aromatic monomers are selected from the groups of phenols or of naphthols.

Several embodiments of our invention are possible. The polymer layer can be built up from a cation-exchanging monomer which has an aromatic OH-containing group containing acidic functionalized groups at the ortho-, meta- or para-position thereof. Advantageously, the acidic functionalized groups are carboxy, sulfonic, phosphinic or phosphonic groups.

Alternatively, the polymer layer can be built up from an ion-exchanging monomer which has an aromatic OH-containing group containing basic functionalized groups at the ortho-, meta- or paraposition thereof. Advantageously, the basic functionalized groups are primary, secondary, tertiary amines, or quaternary ammonium compounds containing the same or different aliphatic groups having one to four carbon atoms. However, the basic functionalized groups of the aromatic monomer from which the polymer is built are linked to the OH-containing monomer by an aliphatic alkylene chain having one to five carbon atoms.

In one embodiment of the invention the polymer can be built up by mixed polymerization or copolymerization of OH-containing monomers mentioned above with cross-linkable OH-containing aromatic monomer. Advantageously, this noncross-linkable monomer contains at least one aliphatic group with two to seven carbon atoms. Advantageously, the electrochemical preparation and deposition occurs on an electrically conductive substrate, which is connected to an electrical source to form an anode. In the process according to our invention the thickness of the polymer layer is controlled by the charge, which is consumed during the electrochemical polymerization, to achieve a thickness of 50 nanometers to 500 micrometers. The electrolyte solution may contain an adherence promoting agent. The cross-linking of the polymer layer may be achieved by heating or by irradiating.

Our invention also comprises the use of the polymer layer either as a semipermeable membrane within an electrode/membrane unit, as a selective layer or as component of a selective layer for potentiometric and amperometric sensors, which are made according to the above-described procedure. Our process also allows the use of the polymer layer as a solid polymer electrolyte.

In the process according to our invention the formation of the polymer layers is carried out electrochemically in an electrolytic bath and results in development of very thin and pinhole free layers with uniform layer thickness which are in situ deposited on the electrically conductive substrate connected as an anode. In keeping with the above polymer layer, the presence of OH-containing aromatic units which bear basic or acidic functionalized groups in the polymer matrix provides the membrane with charge-selective ion exchange and ion conducting capabilities. The concentration of the basic and acidic functionalized groups is controlled by the portion of OH-containing, noncross-linkable aromatic units. Furthermore, the cross-linking degree in the polymer layer is determined by the portion of OH-containing, cross-linkable aromatic units. This leads to an optimization of the semipermeable polymer layer as to its selectivity to species to be separated.

The use of an OH-containing aromatic monomer which does not bear any basic or acidic functionalized substituents for the production of a permeable polymer film is described in the Literature in Anal. Chem. (1987), pp. 1758-1761. The polymer film used exhibits a permeability to small ions, especially $H^+$, $Fe^{2+}$ and Br. It is reported, that the permeability is exclusively dependent upon the size of the Stokes radii of the species. Thereafter, the species discrimination concerning their charge has not been considered. Because this is a different discriminating mechanism compared to that which our invention is based on, it could not be expected that the use of OH-containing aromatic monomers which bear acidic and basic functionalized groups will result in a preparation of a polymer film exhibiting charge-selective and semipermeable ion-exchange capabilities.

DETAILED DESCRIPTION OF THE INVENTION

The polymer layers used according to our invention are built-up of poly(oxyphenylene) or poly(naphthylene) chains, both phenylene and naphtylene units, respectively, bearing ion-exchanging and ion-conducting acidic or basic functionalized groups in ortho-, meta-, or para-position. Acidic functionalized groups suitable for the preparation of a cation-exchanging and cation-conducting membrane are the carboxy (—COOH), sulfonic, (—$SO_3H$), phosphinic and phosphon groups, advantageously carboxy or sulfonic groups. The suitable cation-exchanging monomers may be 4-hydroxyhenzenesulfonic acid, 3-hydroxyhenzoic acid, 4,5-dihydroxynaphthaline-2, 7-disulfonic acid.

The basic functionalized groups suitable for the preparation of an anion-exchanging and anion-conducting membrane are primary (—$NH_2$):, secondary (—$NHR_1$), tertiary amines (—$NR_1R_2$), and quaternary ammonium compounds (—$NR_1R_2R_3$), which are connected to the OH-containing aromatic group by aliphatic alkylene groups having one to five carbon atoms, advantageously one to two carbon atoms. The saturated aliphatic groups $R_1$, $R_2$, and $R_3$ of the amines or ammonium units can be the same or different. The saturated aliphatic groups have a length of from one to four carbon atoms, advantageously one to two carbon atoms. Advantageously the anion-exchanging monomers may be trimethyl-[2-[4-hydroxyphenylene) ethyl ammonium chloride and N1N-dimothyl-3-(4-hydroxyphenylene)-ethyl amine.

The polymerization of the ion-exchanging monomers is carried out electrochemically. During that process, the polymer layers with a linear or nonlinear structure are formed. The position of the functionalized groups on the aromatic part of the chain determinates the structure of the polymer. The polymer layers as manufactured exhibit by themselves ion-exchanging and ion-conducting capabilities without any addition of comonomers. Several embodiments of our invention are possible.

The selectivity of the resulting semipermeable polymer to the exchangeable species can be optimized in situ during the electrochemical formation of the polymer layer. That optimization can be attained by addition of aromatic, noncross-linkable OH-containing comonomers to the electrolytic bath besides the ion-exchanging monomers. The noncross-linkable comonomers have to have at least one aliphatic group with two to seven carbon atoms, advantageously up to four carbon atoms, which is present at the ortho-, meta-, or paraposition, preferably at the ortho-position in order to build up a linear polymer structure. Monomers like o-cresol, 2-ethylphenol, 2-isopropylphenol can be used as comonomers besides the ion-exchanging monomers. The comonomers can be added to the electrolytic bath up to a proportion of 84 Mol % relative to the total monomer concentration.

The permeability of the resulting semipermeable polymer layer to the exchangeable species can also be optimized in situ during the electrochemical deposition of the polymer layer. The optimization can be attained by addition of aromatic, cross-linkable OH-containing comonomers to the electrolytic bath besides the ion-exchanging monomers. Advantageously the aromatic group of the comonomer has an aliphatic group with up to seven carbon atoms, advantageously up to four carbon atoms. This aliphatic group is advantageously unsaturated. A suitable, unsaturated aliphatic group has the length of from two to seven, advantageously two to four carbon atoms, and is advantageously a vinyl or allyl group. An appropriate comonomer may be the 2-allylphenol. Advantageously the aliphatic group of the comonomer is placed in the ortho-position. The aromatic, cross-linkable OH-containing comonomers can be added besides the ion-exchanging monomers up to a proportion of 50 Mol % relative to the total monomer concentration to the electrolytic bath.

In examples 3 and 4 (to be discussed hereafter), it is illustrated, that the diffusion coefficient, which is a measure of the permeability for species to be separated, can be controlled. That control is attained by adjustment of the concentration of the cross-linkable OH-containing aromatic component in the monomer solution. The cross-linkable OH-containing aromatic component used was 2-allylphenol. Hence, the diffusion coefficient within the membrane decreases with an increasing concentration of the cross-linking component.

The electrochemical deposition of ion-selective polymer layers occurs in acidic or in basic media. The electrochemical deposition of cation-selective polymer layers is performed by anodic oxidation of the monomers at the substrate, advantageously in aqueous alkaline media. The electrolyte solution contains an amine besides the monomer in order to suppress the passivation of the electrode surface. Advantageously the amine is a primary amine with an aliphatic group. The aliphatic group is advantageously an alkyl group with one to ten carbon atoms, which can be unsaturated. Suitable amines include the allylamine and propylamine.

The electrochemical deposition of anion-selective polymer layers occurs by anodic oxidation of the monomers at the substrate, advantageously in aqueous acidic media. The electrolyte solution used contains, besides the monomer, an acid and salt of the acid which suppress the passivation of the electrode surface. Advantageously the acid is a dicarbonic acid and the salt is a diammonium compound of the dicarbonic acid. Suitable compounds include the oxalic acid and diammonium oxalate for the formation of the polymer layers. Advantageously a water-alcohol mixture is used, which has a mixture ratio of 1:10 to 10:1 by volume, advantageously 1:5 to 5:1 by volume. An aliphatic alcohol of low molecular weight is advantageously utilized.

Advantageously the electrolyte solution contains an adhesion promoting agent, which promotes the adherence of the formed polymer to the electrolyte surface. Suitable adhesion promoting agents are the ethylene glycol monobutyl ether or ethylene glycol monomethyl ether. The adhesion promoting agent can be used up to a proportion of one to ten vol % of the electrolyte solution. Advantageously, the electrochemical oxidation occurs preferentially potentiostatically by applying a triangular voltage sweep in the range of 0 to 6 Volts, or advantageously within the potential range of 0 to 2 Volts vs. saturated calomel electrode (reference) by applying a scan rate of 0.5 to 200 mV/s, advantageously 5 to 100 mV/s. The electrochemical deposition is processed at 20° to 50° C., especially at room temperature.

The thickness of the polymer layer is controlled during the electrochemical deposition by means of the charge consumed in the anodic polymerization reaction. For the charge control during the formation of the polymer on the electrode, a theoretical columbic efficiency of 4F/Mol per OH-containing aromatic monomer is assumed. After the electrochemical deposition of the firmly adhering polymer layer to the substrate, the layer must be cross-linked by the unsaturated groups present in the film by heating or irradiation. Advantageously, a thermal treatment, i.e., heating at 60° to 150° C., preferably at 80° to 150° C. is performed. A suitable temperature may be easily determined by conducting suitable simple experiments with a given polymer layer. An irradiation treatment with UV-radiation is also possible.

The thickness of the membrane is in the range of 50 nanometers to 500 micrometers, advantageously from 100 nanometers to 10 micrometers, preferably in the range of 100 nanometers to 1 micrometers. It has been found that membranes with a layer thickness in this range provides the desired cation- and anion-exchanging capabilities and a high permeability to the species to be separated. The diffusion coefficients of the species to be separated within the prepared membrane is slightly lower than those present in the electrolyte. Therefore, the substrate coated with the membrane of our invention can be used in such processes, in which substrates coated by the techniques of prior art (i.e., dip-coating process) cannot be employed hitherto due to the extremely low permeability of the species within the membrane.

According to one advantageous use of our invention, the polymer layers can be applied as charge-selective and cation-and anion-conducting membranes in an electrode/membrane unit. An electrode, which electroactive area is equipped with a charge-selective and cation- or anion-conducting polymer layer, can be employed to charge-exchanging composite electrode or used in electrochemical processes or in electrochemical devices (Bogenschutz/Krusenmark; Elektrochemische Bauelemente; Verlag Chemie, Weinheim, 1976).

According to another advantageous use of our invention, the polymer layer can be employed as a selective layer or as a component of a selective layer of electrodes, which are used as potentiometric or amperometric sensors (Cammann, Das Arbeiten mit ionenselektiven Elektroden; Springer-Verlag, Berlin, 1977; J. Janata, The Principles of Chemical Sensors, Plenum Press, New York, 1989).

According to still another advantageous use of our invention the polymer layers can be used as solid polymer electrolyte, which are employed in electrolytic cell to separate the anolyte compartment from the catolyte compartment of the cell or to eliminate interfering reactions during the electrochemical processes.

Our invention is illustrated in more detail by the following examples:

Example 1

A cation-exchanging and cation-conducting membrane was polymerized and deposited on the electroactive area of electrical conducting substrates. As electrode materials, nobel metals (i.e., platinum or gold) or composite materials, (i.e., carbon-polyethylene, or carbon fiber with a diameter of 8 micrometer) were employed. The following electrolyte solution was used:

| | |
|---|---|
| 0.23 Mol/l | 3-Hydroxybenzoic acid |
| 0.4 Mol/l | Allylamine |
| 0.2 Mol/l | Cellosolve (Ethylenglycol monobuthylether) |

This was dissolved in Methanol and Water 1:1 (volume proportions).

The electrochemical polymerization was performed potentiostatically by applying a triangular voltage sweep in the range of 0 to 1 Volt vs. saturated calomel electrode at room temperature. After a single triangular sweep with a start and final potential of 0 Volt vs. saturated calomel electrode, the polymer layer deposited on the electrodes was heated in an oven at 80° C. for approximately 15 to 30 minutes in order to remove possibly remaining electrolyte. The polymer layer formed has a layer thickness of approximately 0.8 micrometers and exhibits cation-exchanging and cation-conducting behavior. Anions, like $Fe(CN)_6^{3-}$ or $J^-$, were totally screened out by the semipermeable membrane. Consequently, these coated electrodes did not show any electrochemical activity to the above-mentioned anions. The neutral species could be detected.

Example 2

Again a cation-exchanging and cation-conducting membrane was polymerized and deposited on the electroactive area of electrical conducting substrates. As electrode materials, the metals mentioned in example 1 were employed. The following electrolyte solution was used:
This was dissolved in Methanol and Water 1:1 (volume proportions).

The electrochemical polymerization was performed according to example 1. Afterwards, the polymer layer deposited on the electrodes was heated in an oven at 80° to 100° C. for approximately 15 to 30 minutes in order to crosslink the polymer and to remove electrolyte which possibly remained. The polymer layer formed has a layer thickness of approximately 0.5 micrometers and exhibits cation-exchanging and cation-conducting behavior. As described in example 1 anions, like $Fe(CN)_6^{3-}$ or $J^-$, were totally screened out by the semipermeable membrane. No electrochemical activity of the anions could be detected by using these coated electrodes. In comparison to an uncoated electrode and to the electrodes coated according to example 1, the selectivity to large cations, like $Ru(NH_3)_6^{3+}$, could be improved. An increase of diffusion limiting current for the reduction of $Ru(NH_3)_6^{3+}$ dissolved in solutions could be observed. For small cations, i.e., $Fe^{2+}$, the accumulation effect was not observed.

Example 3

Again a cation-exchanging and cation-conducting membrane was polymerized and deposited on the electroactive area of electrical conducting substrates. As electrode materials, the metals mentioned in example 1 were employed. The following electrolyte solution was used:

| | |
|---|---|
| 0.23 Mol/l | 4-Hydroxybenzenesulfonic acid |
| 0.003 Mol/l | 2-Allylphenol |
| 0.03 Mol/l | Allylamine |
| 0.2 Mol/l | Cellosolve (Ethylenglycol monobuthylether) |

This was dissolved in Methanol and Water 1:1 (volume proportions).

The electrochemical polymerization and the following heat treatment were performed according to example 2. The polymer layer formed has a layer thickness of approximately 0.15 micrometers and exhibits cation-exchanging and cation-conducting behavior. Also in this example, electrochemically active anions do not reach the electrode surface. They could not be detected amperometrically, although, the layer thickness was reduced to approximately 70% when compared to those given in example 1 and 2. The diffusion coefficient of $Ru(NH_3)_6^{3+}$ within the membrane was determined to $D_o = 4.4 \ 10^{-6} cm^2/s$. This value is only slightly lower than that of $Ru(NH_3)_6^{3+}$ in solution ($D_o = 5.5 \ 10^{-6} cm^2/s$).

Example 4

Again a cation-exchanging and cation-conducting membrane was polymerized and deposited on the electroactive area of electrical conducting substrates. As electrode materials, the metals mentioned in example 1 were employed. The following electrolyte solution was used:

| | |
|---|---|
| 0.23 Mol/l | 4-Hydroxybenzenesulfonic acid |
| 0.08 Mol/l | 2-Allylphenol |
| 0.03 Mol/l | Allylamine |
| 0.2 Mol/l | Cellosolve (Ethylenglycol monobuthylether) |

This was dissolved in Methanol and Water 1:1 (volume proportions).

The electrochemical polymerization and the following heat treatment were performed according to example 2. The polymer layer formed has a layer thickness of approximately 0.1 micrometers and exhibits cation-exchanging and cation-conducting behavior. Electrochemically active anions could not be detected amperometrically. The diffusion coefficient of $Ru(NH_3)_6^{3+}$ within the membrane was determined to $D_o = 2.3 \ 10^{-6} cm^2/s$. In comparison to example 3 the membrane permeability to the species to be separated was reduced by a factor of 0.5. due to the increase of the cross-linking degree.

Example 5

An anion-exchanging and anion-conducting membrane was polymerized and deposited on the electroactive area of electrical conducting substrates. As electrode materials, the metals mentioned in example 1 were employed. The following electrolyte solution was used:

| | |
|---|---|
| 0.23 Mol/l | Trimethyl-[2-(4-hydroxyphenyl) ethyl] ammonium choloride |
| 0.003 Mol/l | 2-Allylphenol |
| 0.4 Mol/l | Allylamine |
| 0.2 Mol/l | Cellosolve (Ethylenglycol monobuthylether) |

This was dissolved in Methanol and Water 1:1 (volume proportions).

The electrochemical polymerization was performed potentiostatically by applying a triangular voltage sweep in the range of 0 to 2 Volt vs. saturated calomel electrode at room temperature. After a single triangular sweep with a start and final potential of 0 Volt vs. saturated calomel electrode, the polymer layer deposited on the electrodes was heated in an oven at 80° to 100° C. for approximately 15 to 30 minutes in order to crosslink the polymer and to remove the electrolyte which possibly remained after deposition. The polymer layer formed has a layer thickness of approximately 0.3 micrometers and exhibits anion-exchanging and anion-conducting behavior. Cations, like $Ru(NH_3)_6^{3+}$, $Ag^+$, or $Fe^{2+}$ were totally screened out by the semipermeable membrane. They could not be detected potentiostatically using the electrodes coated according to our invention.

Example 6

Again an anion-exchanging and anion-conducting membrane was polymerized and deposited on the electroactive area of electrical conducting substrates. As electrode materials, the metals mentioned in example 1 were employed. The following electrolyte solution was used:

| | |
|---|---|
| 0.23 Mol/l | Ethyl-dimethyl-[2-(4-hydroxyphenyl) ethyl] ammonium chloride |
| 0.2 Mol/l | Oxalic acid |
| 0.1 Mol/l | Diammonium oxalate |
| 0.2 Mol/l | Methylcellosolve (Ethylenglycol monomethylether) |

This was dissolved in Methanol and Water 1:1 (volume proportions).

The electrochemical polymerization and the following heat treatment were performed according to example 5. The polymer layer formed has a layer thickness of approximately 0.3 micrometers and exhibits anion-exchanging and anion-conducting behavior like the membrane prepared according to example 5. However, as a result the diffusion coefficient of $Fe(CN)_6^{3-}$ within the membrane is increased by a factor of 2 in comparison to the above-mentioned membrane (example 5).

It will be understood that each of the elements described above, or two or more together, may also find a useful application in other types of electrodes.

While the invention has been illustrated and described as a coating of an electrically conducting substrate, a process for making it and a process for using it, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed is:

1. A process for preparation of a semipermeable polymer layer, said polymer layer having a thickness, exhibiting ion-exchanging capability and ion-conducting capability comprising the steps of:
   (a) producing said polymer layer from an electrolyte bath by electrochemical polymerization of a OH-containing aromatic monomer, which contains acidic or basic functionalized groups;
   (b) depositing in situ said polymer layer on an electrically conducting substrate; and
   (c) subsequently self cross-linking said polymer layer by one of heating and irradiating.

2. A process according to claim 1 wherein step a) comprises producing said polymer layer by copolymerization or mixed polymerization of OH-containing aromatic monomer, which contains acidic or basic functionalized groups, with a noncross-linkable OH-containing aromatic monomer.

3. A process according to claim 1 wherein step a) comprises producing said polymer layer by copolymerization or mixed polymerization of OH-containing aromatic monomer, which contains acidic or basic functionalized groups, with a cross-linkable OH-containing aromatic monomer having an unsaturated aliphatic group at an ortho-position thereof.

4. A process according to claim 1 wherein said OH-containing aromatic monomer is selected from the groups of phenols or of naphthols.

5. A process according to claim 1 wherein said monomer has an aromatic OH-containing group containing acidic functionalized groups at the ortho-, meta- or para-position thereof.

6. A process according to claim 1 wherein said acidic functionalized groups are carboxy, sulfonic, phosphinic or phosphonic groups.

7. A process according to any of claims 1, 2, 3, or 4 wherein said monomer has an aromatic OH-containing group containing basic functionalized groups at an ortho-, meta- or para-position thereof.

8. A process according to claim 1 wherein said basic functionalized groups are primary, secondary, tertiary amines, or quaternary ammonium compounds containing the same or different aliphatic groups having 1 to 4 carbon atoms.

9. A process according to claim 1 further comprising linking said basic functionalized groups to said OH-containing aromatic monomer by an aliphatic alkylene chain having 1 to 5 carbon atoms.

10. A process according to claim 1 wherein said noncross-linkable monomer has an OH-containing aromatic group containing at least one aliphatic group having 2 to 7 carbon atoms.

11. A process according to claim 1 wherein said cross-linkable monomer has an OH-containing aromatic group containing at least one unsaturated aliphatic group having 2 to 7 carbon atoms.

12. A process according to claim 1 further comprising connecting said electrically conducting substrate as an anode during the electrochemical preparation and deposition of said polymer layer.

13. A process according to claim 1 further comprising controlling the thickness of the polymer layer by controlling the charge, which is consumed during the electrochemical polymerization.

14. A process according to claim 1 wherein said polymer thickness is in the range of 50 nanometers to 500 micrometers.

15. A process according to claim 1 wherein said electrolyte bath contains an adherence promoting agent.

16. A process according to claim 1 further comprising performing said cross-linking of said polymer layer by heating or by irradiating.

* * * * *